United States Patent [19]

Ručman et al.

[11] 4,219,555
[45] Aug. 26, 1980

[54] 2-BROMOERGOSINE AND PHARMACOLOGICALLY COMPATIBLE ACID ADDITION SALTS THEREOF AS WELL AS THEIR USE FOR THE TREATMENT OF ARTERIAL HYPERTENSION AND OR HEART ARRYTHMIAS

[75] Inventors: Rudolf Ručman; Nebojša Djordjevic, both of Ljubljana, Yugoslavia

[73] Assignee: LEK Tovarna farmacevtskih in kemicnih izdelkov, N.sol.o., Ljubljana, Yugoslavia

[21] Appl. No.: 932,386

[22] Filed: Aug. 9, 1978

[30] Foreign Application Priority Data

Sep. 9, 1977 [YU] Yugoslavia .................. 2161/77

[51] Int. Cl.² .................. C07D 519/02; A61K 31/495
[52] U.S. Cl. ........................... 424/250; 544/346
[58] Field of Search .............. 544/346; 424/250; 260/285.5

[56] References Cited

U.S. PATENT DOCUMENTS

| | | | |
|---|---|---|---|
| 2,497,214 | 8/1948 | Stoll et al. | 544/346 |
| 3,585,201 | 6/1971 | Arcamone et al. | 260/285.5 |
| 3,752,814 | 8/1973 | Fluckiger et al. | 544/346 |
| 3,755,328 | 8/1973 | Stadler et al. | 544/346 |
| 3,883,655 | 5/1975 | Foxe | 429/261 |
| 3,920,664 | 11/1975 | Clemens et al. | 260/285.5 |
| 4,124,712 | 11/1978 | Stütz et al. | 544/346 |
| 4,138,565 | 2/1979 | Ehrhardt et al. | 544/346 |

FOREIGN PATENT DOCUMENTS

2752532  6/1978 Fed. Rep. of Germany .

OTHER PUBLICATIONS

Troxler et al., Helv. Chim. Acta., vol. 40, pp. 2460–2470 (1957).

Primary Examiner—Mary C. Lee
Attorney, Agent, or Firm—Pollock, Vande Sande and Priddy

[57] ABSTRACT

2-Bromoergosine of the formula:

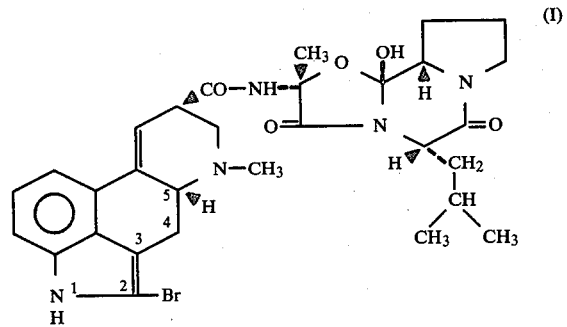

and acid addition salts thereof. The acid addition salts are employed in the treatment of arterial hypertension and of heart arrythmias.

6 Claims, No Drawings

2-BROMOERGOSINE AND PHARMACOLOGICALLY COMPATIBLE ACID ADDITION SALTS THEREOF AS WELL AS THEIR USE FOR THE TREATMENT OF ARTERIAL HYPERTENSION AND OR HEART ARRYTHMIAS

The subject of the present invention is new 2-bromoergosine and its physiologically compatible acid addition salts, a process for the preparation thereof as well as their use in medicines for the treatment of arterial hypertension and heart arrythmias.

2-bromoergosine according to the invention is represented by the formula

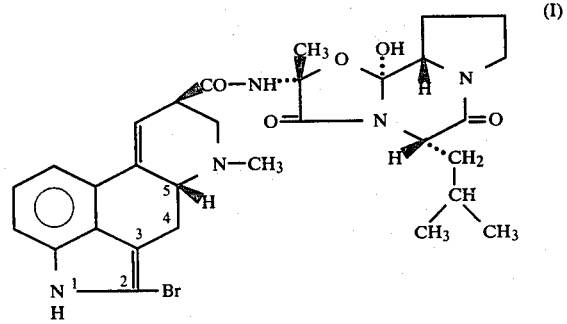

and a process for the preparation thereof is characterized in that the natural alkaloid ergosine is selectively brominated in 2-position.

The selective bromination is carried out e.g. with pyrrolidone hydrotribromide, with N-bromo compounds, with dioxan dibromide or with 3-bromo-4,5-dialkyl-2-oxazolidinones. The reaction is carried out at ambient or at slightly elevated temperature in a solvent that is inert at reaction conditions and optionally at the addition of a radical initiator, such as 2,2'-azo-bis(2-methylpropio-nitrile) [cf. Bianchi G., Grünanger P., Tetrahedron 21, 817 (1965)] in an inert atmosphere.

When using N-bromo compounds and dioxan dibromide, the yields are moderate. As the reaction takes more than 10 hours at ambient temperature, it is accelerated by heating to 40° to 50° C. or by adding catalytic amounts of the radical initiator. On the other hand, the elevation of temperature is inconvenient because by-products are formed.

The most convenient bromination at ambient temperature is made possible by pyrrolidone hydrotribromide. It is used in an amount of 1 to 1.5 moles per 1 mole of ergosine. Cyclic ethers, such as dioxan or tetrahydrofuran, or chlorinated hydrocarbons, such as chloroform or methylene chloride, are used as reaction solvents.

In practice, the reaction is carried out in such a way that to an ergosine solution pyrrolidone hydrotribromide, dissolved in the same solvent, is added at room temperature, in an inert atmosphere and under stirring. The reaction is completed as soon as the reactants are thoroughly blended.

The starting ergosine is a known natural compound, which is isolated by extraction of ergots. The pyrrolidone hydrotribromide is an easily available commercial product.

For therapeutic use, 2-bromoergosine is converted into its acid addition salt with a physiologically acceptable inorganic or organic acid. Hydrochloric acid, hydrobromic acid, sulfuric acid, phosphoric acid, formic acid, acetic acid, diethylacetic acid, propionic acid, malic acid, lactic acid, fumaric acid, maleic acid, methansulfonic acid, ethansulfonic acid, tartaric acid, citric acid etc. can be used for that purpose.

2-bromoergosine according to the invention and its physiologically compatible acid addition salts exhibit the following pharmacological properties.

1. Acute Toxicity

The mean lethal dose $DL_{50}$ was determined in mice of both sexes weihging from 18 to 25 g. By means of a metal gastric probe, the mice were orally administered 2-bromoergosine methansulfonate in an amount of 0.01 ml/g of body weight. The mean lethal dose $DL_{50}$, calculated by the method of Litchfield J. T. and Wilcoxon P., J. Pharmacol. exp. Ther. 96, 99 (1946), and the confidence interval of 95% amounted to 489.7 (427.2 to 561.4) mg/kg.

2. The Effect on Arterial Pressure (a) The effect on blood pressure of normotensive narcotized rats The artery Carotis communis in narcotized rats (variety Wistar) was cannulated and the blood pressure was recorded on a dynograph (type Beckmann) over a mini-transducer. The frequency of heart pulsation was recorded by a cardiotachometer on the same dynograph.

2-bromoergosine methansulfonate was administered intravenously into Vena jugularis by means of an apparatus for slow infusion (B. Melsungen) in doses of 10, 20, 50, 150, 450, 1500, and 4500 mg/kg of body weight.

The results in Table 1 show that by increasing the dose, a greater systolic or diastolic pressure drop was achieved, whereas the pulse pressure increased.

Table 1

| Intravenous dose in mcg/kg of body weight | The change (%) in | | |
|---|---|---|---|
| | systolic pressure | diastolic pressure | pulse pressure |
| 10 | 7.41 ↓ | 14.16 ↓ | 13.34 ↑ |
| | ±1.56 | ±2.68 | ±2.23 |
| 20 | 8.57 ↓ | 17.09 ↓ | 12.77 ↑ |
| | ±1.54 | ±2.23 | ±6.41 |
| 50 | 11.61 ↓ | 21.52 ↓ | 15.43 ↑ |
| | ±2.06 | ±2.83 | ±1.70 |
| 150 | 14.13 ↓ | 25.33 ↓ | 23.81 ↑ |
| | ±1.88 | ±6.23 | ±10.86 |
| 450 | 19.46 ↓ | 39.22 ↓ | 33.33 ↑ |
| | ±2.54 | ±2.48 | ±9.11 |
| 1500 | 22.32 ↓ | 46.98 ↓ | 41.49 ↑ |
| | ±1.50 | ±1.30 | ±8.70 |
| 4500 | 19.38 ↓ | 45.49 ↓ | 37.96 ↑ |
| | ±0.71 | ±1.93 | ±6.91 |

↓ = systolic or diastolic pressure drop
↑ = pulse pressure rise

All doses caused the inhibition of the hypertensive reflex of the carotide sinus and it came to a depression of the pressure rise, which had been caused by the unilateral occlusion of the artery Carotis communis.

(b) The effect on pressure drop in rats with a cut spinal cord

Rats (variety Wistar) in urethane narcosis were spinalized (their spinal cord was cut in the region of the second cervical vertebra) and connected to an artificial breathing apparatus (B. Melsungen). By this intervention the central regulation of blood pressure was eliminated. A blood pressure drop for about 50 mm Hg took place. This experiment was supposed to show whether the examined compound directly affected the smooth muscles of blood vessels.

The results of experiments showed that 2-bromoergosine methansulfonate effected a change in blood pressure only in intravenous doses of 450 mcg/kg by raising it to normal blood pressure. Thus, the compound has a similar effect as dihydroergotoxine and dihydroergotamine, i.e. a vasoconstrictory effect, and it causes the contraction of smooth muscles of blood vessels [Rothlin E., Cerletti A., Verh. dtsch. Ges. Kreislaufforsch. 15, 158 (1949)].

(c) The effect on adrenalin hypertension in narcotized rats

As a control part of the experiment, in rats (variety Wistar) that were narcotized by urethane and prepared for the recording of blood pressure, a short hypertension was caused by a double intravenous administration of adrenalin in doses of 10 mcg/kg, then 2-bromoergosine methansulfonate was infused in doses of 10, 20, 50, 150, 450, 1500, and 4500 mcg/kg and after 3 minutes adrenalin was repeatedly administered in the same doses as above.

The minimum inhibitory doses of 2-bromoergosine methanesulfonate amounted to 10 mcg/kg only. At great doses an inversion of the adrenalin effect took place. The experiments showed that 2-bromoergosine methanesulfonate inhibited the adrenalin effect on blood pressure with approximately the same intensity as dihydroergotoxine and dihydroergotamine. This effect is probably the result of competitive antagonism between 2-bromoergosine methanesulfonate and adrenalin to $\alpha$-adrenergic receivers [Bricher R., Cerletti A., Helv. med. Acta 16, Suppl. 22 (1949)].

(d) The effect on hypertension caused by serotonin in rats with a cut spinal cord Spinalized rats (their spinal cord was cut in the region of the second cervical vertebra) of the variety Wistar were used.

The results of experiments showed that 2-bromoergosine methanesulfonate, administered intravenously in a dose of 150 mcg/kg, visibly reduced the effect of serotonin when compared with the control effect of this compound. In this dose, 2-bromoergosine methanesulfonate has a similar effect as dihydroergotoxine and dihydroergotamine.

(e) The effect in normotensive rats

For the experiment 10 normotensive rats (variety Wistar) of both sexes, weighing from 200 to 250 g, were used each time. 2-bromoergosine methanesulfonate was administered intraperitoneally in doses of 5 mcg/kg/day and systolic blood pressure was measured. Blood pressure dropped step by step from the starting level of 123 to 127 mm Hg until after 8 to 10 days it reached a level of about 95 to 105 mm Hg and remained at that level to the end of the experiment, i.e. for 30 days.

(f) The effect in spontaneously hypertensive rats

For this experiment groups of 10 spontaneously hypertensive rats (variety Okamoto Aoki $F_{30}$) of both sexes, weighing from 200 to 250 g, were used. 2-bromoergosine methanesulfonate was administered intraperitoneally in doses of 5 mcg/kg/day and blood pressure was measured. Systolic blood pressure dropped in 6 to 10 days from the starting level of 174 to 177 mg Hg to about 135 to 140 mm Hg and remained at that level to the end of the experiment, i.e. for 30 days, though the treatment was continued.

(g) The effect in DOCA-hypertensive rats

In young rats (variety Wistar) of both sexes, weighing 40 g, hypertension was caused by unilateral nephrectomy and subsequent feeding of the animals with standard industrial food and water solution of sodium chloride (1 w/vol %) ad libitum.

7 Days after unilateral nephrectomy, the rats were intramuscularly administered 38 mg/kg of DOCA (DOCA=deoxycorticosteroidacetate) in the form of a 1 w/vol % microsuspension in 0.5 w/vol % solution of the formulation Tween 80, to which carboxymethylcellulose (0.5 w/vol %) was added, twice per week. DOCA was administered for 6 weeks when systolic pressure achieved its maximum value, and subsequently the intraperitoneal administration of 2-bromoergosine methanesulfonate began.

In the control group of animals the blood pressure remained increased for only 2 to 3 weeks and then dropped to 135 mm Hg. In rats treated with 2-bromoergosine methanesulfonate, however, blood pressure dropped step by step since the very beginning of the treatment. After 10 to 12 days, it achieved the greatest drop from the starting level of 184 to 187 mm Hg to about 135 to 140 mm Hg, with regard to the control group.

The difference between both groups was then reduced because of the above-mentioned spontaneous dropping of blood pressure in the control group.

3. The Effect of 2-bromoergosine on Heart

In experiments in normotensive narcotized rats with intact and with cut spinal cord, 2-bromoergosine methanesulfonate in active doses caused bradycardia. This effect can be established in all known ergot alkaloids and derivatives thereof [Rothlin E., Wien. Klin. Wschr. 62, 893 (1950)].

The effect of 2-bromoergosine methanesulfonate on heart in vitro was examined on isolated heart of a guinea pig by the modified Langendorff's method [Zalar S., Bano M., Djordjević N., Kozjak F., Boll. Chim. Farmac. 114, 146 (1975)]. 2-bromoergosine methanesulfonate was infused by an apparatus for slow infusion (B. Melsungen). The results are shown in Table 2.

Table 2

| Compound | Dose in mcg/g of heart | Maximum positive inotropic effect | Maximum negative chronotropic effect |
|---|---|---|---|
| 2-bromoergosine methanesulfonate | 0.70 | 80% | 29% |
| dihydroergotoxine | 0.85 | 7% | 5% |
| dihydroergotamine | 0.72 | 60% | 10% |
| ergotamine | 0.65 | 75% | 30% |

From the above results it is evident that 2-bromoergosine has an effect on isolated heart, which is qualitatively and quantitatively similar to that of ergotamine.

On the basis of the described pharmacological properties, it can be established that 2-bromoergosine has a hypertensive effect, as shown by experiments in normotensive rats, in spontaneously hypertensive rats and in DOCA-hypertensive rats, 2-bromoergosine affects the contraction of the heart ventricle (positive inotropic effect) and the frequency of heart pulsation (negative chronotropic effect), 2-bromoergosine inhibits blood pressure rise under the influence of adrenalin and serotonin.

On the basis of these properties, 2-bromoergosine can be used in treatment of arterial hypertension and of heart arrythmias.

2-bromoergosine in the form of its physiologically compatible acid addition salts is used as a medicine for enternal and parenteral administration. The pharmaceutical compositions are formulated by adding inorganic and organic adjuvants. For tablets and dragées there are added e.g. lactose, starch, talc, stearates etc. For solutions and suspensions there are added e.g. water, alcohols, glycerine, vegetable oils etc. For suppositories there are added e.g. natural oils, hardened oils and waxes. The formulations can also contain suitable preservatives, stabilizers, surfactants, dissolving intermediaries, sweetening agents and dye stuffs.

A suitable daily dose for 2-bromoergosine in the form of its physiologically compatible acid addition salts amounts to 0.005 to 0.02 mg/kg of body weight for intravenous administration and to 0.05 to 0.3 mg/kg of body weight for oral administration, calculated for pure 2-bromoergosine.

EXAMPLE 1

N-bromosuccinimide (3.52 g, 19.8 mmoles), dissolved in dioxan (60 ml), is added to the solution of ergosine (9.54 g, 17.4 mmoles) in dioxan (180 ml) under stirring in an inert atmosphere. The reaction lasts 10 minutes at 40° C. Then the reaction mixture is dried in vacuo. The residue is distributed in a separating funnel between sodium carbonate (200 ml of 2 N water solution) and methylenechloride (300 ml). The water phase is extracted three times with methylenechloride (150 ml each time). Methylenechloride extracts are combined and dried in vacuo. The residue is dissolved in methylenechloride (40 ml) and is separated by chromatography on a column which is packed with neutral aluminum oxide (1180 g) having an activity of II to III according to Brockmann. The elution is carried out with methylenechloride containing ethanol (0.2 vol/vol %). Fractions containing 2-bromoergosine are dried in vacuo. The dry substance is crystallized from ethylacetate. Pure crystal 2-bromoergosine (4.33 g; 34.8% of the theory) is obtained, having the composition $C_{30}H_{36}N_5O_5Br \cdot CH_3COOC_2H_5$. It has a melting point of 183° to 185° C. (decomposition) and a specific rotation of $[\alpha]_D^{20} = -91.6°$ (c=1, chloroform).

Elementary analysis for $C_{30}H_{36}N_5O_5Br$—Found: C 57.63%, H 6.06%, N 10.84%, Br 12.40%; Calc.: C 57.51%, H 5.79%, N 11.18%, Br 12.73%.

EXAMPLE 2

A solution of pyrrolidone hydrotribromide (6.94 g, 14 mmoles) in dioxan (1500 ml) is added to a solution of ergosine (5.47 g, 10 mmoles) in dioxan (200 ml) under stirring at ambient temperature in an inert atmosphere. The reaction is completed as soon as both reactants are blended. The reaction mixture is dried in vacuo. The residue is purified by means of distribution between the water phase and the organic phase and by column chromatography as in Example 1. 2-bromoergosine in the form of ethylacetate crystals (5.81 g; 81.3% of the theory) is obtained. The compound has the same characteristics as in Example 1.

EXAMPLE 3

A solution of pyrrolidone hydrotribromide (6.94 g, 14 mmoles) in methylenechloride (300 ml) is added to a solution of ergosine (5.47 g, 10 mmoles) in methylenechloride (100 ml) under stirring at ambient temperature in an inert atmosphere. The reaction mixture is concentrated to a half of its volume and it is extracted three times with sodium carbonate (200 ml of 2 N water solution each time). The methylenechloride solution is separated by chromatography on a column with silica gel and eluted with methylenechloride, to which dioxan (0 to 20 vol/vol %) is gradually added. The fractions containing 2-bromoergosine are dried and crystallized from ethylacetate. 2-bromoergosine (5.06 g; 70.7% of the theory) is obtained in the form of ethylacetate crystals. The compound has the same characteristics as in Example 1.

EXAMPLE 4

Amorphous 2-bromoergosine (2.42 g, 3.86 mmoles, precipitated from petroleum ether) is dissolved in ethanol (20 ml) containing methanesulfonic acid (0.22 ml, 4.24 mmoles) and, under stirring, the solution is poured into diethyl-ether (400 ml). After the filtering and drying of the precipitate, the easily water-soluble 2-bromoergosine methanesulfonate (2.49 g; 89.4% of the theory) is obtained. It has a melting point of 191° to 192° C. and a specific rotation $[\alpha]_D^{20} = +104°$ (c=1, chloroform).

EXAMPLE 5

| Tablets Composition | mg/tablet |
| --- | --- |
| 2-bromoergosine methansulfonate | 20 |
| lactose | 228 |
| starch | 27 |
| talc | 13 |
| tragacanth | 10 |
| magnesium stearate | 2 |
| | 300 mg |

By means of standard methods, the active substance is blended with other ingredients, granulated and pressed into tablets.

EXAMPLE 6

| Capsules Composition | mg/capsule |
| --- | --- |
| 2-bromoergosine methanesulfonate | 20 |
| lactose | 280 |
| | 300 mg |

By means of standard methods, the active substance is blended with lactose and filled into capsules.

EXAMPLE 7

Injection solution

| Composition | weight in mg |
| --- | --- |
| 2-bromoergosine methanesulfonate | 1.00 |
| sodium carboxymethylcellulose | 1.50 |
| polyvinyl pyrrolidone | 5.50 |
| lecithin | 3.20 |

-continued

| Composition | weight in mg |
|---|---|
| benzyl alcohol | 0.01 |
| buffer | q.s. |
| bidistillated water | ad 1 ml |
| | 1 ml |

The solution is prepared by means of standard methods, it is sterilized and filled into ampules.

What is claimed is:

1. A medicine for the treatment of arterial hypertension or of heart arrythmias or both comprising a pharmacologically active amount of physiologically compatible acid addition salt of 2-bromoergosine of the formula I:

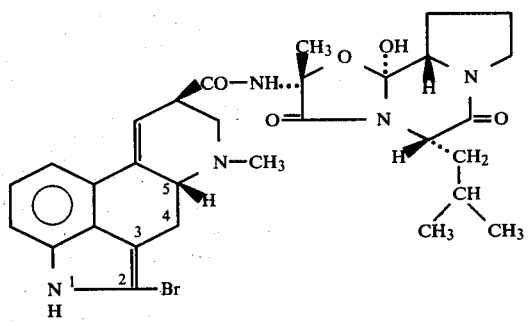

2. A process for the treatment of arterial hypertension or of heart arrythmias or both comprising the administration of a pharmacologically active amount of physiologically compatible acid addition salt of 2-bromoergosine of the formula I:

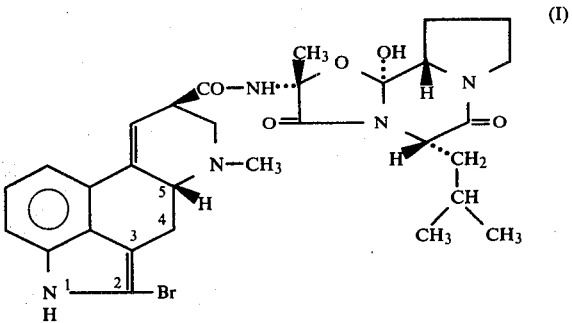

3. The medicine of claim 1 wherein said salt is 2-bromoergosine methane sulfonate.

4. The process of claim 2 wherein said salt is 2-bromoergosine methane sulfonate.

5. The process of claim 2 wherein the salt is administered by intravenous administration at daily dosage calculated as 2-bromoergosine of 0.005 to 0.02 mg/kg of body weight.

6. The process of claim 2 wherein the salt is administered by oral administration at daily dosage calculated as 2-bromoergosine of 0.05 to 0.3 mg/kg of body weight.

* * * * *